United States Patent [19]

Hutchison et al.

[11] Patent Number: 5,174,915

[45] Date of Patent: * Dec. 29, 1992

[54] MEDIUM SPEED DIESEL ENGINE LUBRICATING OILS

[75] Inventors: David A. Hutchison, Naperville; Richard D. Stauffer, St. Charles, both of Ill.

[73] Assignee: Ethyl Petroleum Additives, Inc., Richmond, Va.

[*] Notice: The portion of the term of this patent subsequent to Mar. 13, 2007 has been disclaimed.

[21] Appl. No.: 791,076

[22] Filed: Nov. 12, 1991

Related U.S. Application Data

[63] Continuation of Ser. No. 103,170, Sep. 30, 1987, abandoned.

[51] Int. Cl.$^5$ .......................................... C10M 133/44
[52] U.S. Cl. .................................... 252/50; 252/51.5 A
[58] Field of Search ........................... 252/50, 51.5 A

[56] References Cited

U.S. PATENT DOCUMENTS

| | | | |
|---|---|---|---|
| 3,272,746 | 9/1966 | Le Suer et al. | 252/51.5 A |
| 3,341,542 | 9/1967 | Le Suer et al. | 252/47.5 |
| 4,908,145 | 3/1990 | Fenoglio | 252/51.5 A |

*Primary Examiner*—Ellen McAvoy

[57] ABSTRACT

There is provided a lubricating oil composition for use in medium speed diesel engines, such as railroad locomotive diesel engines. This lubricating oil composition comprises an oil of lubricating viscosity and a minor amount of a reaction product that is obtained by reacting an alkyl-substituted dicarboxylic acid compound selected from the group consisting of alkyl-substituted dicarboxyic acids, alkyl-substituted dicarboxylic acid anhydrides, and mixtures thereof with a basic salt of aminoguanidine under selected conditions that will provide a product rich in alkyl bis-3-amino-1,2,4-triazole.

1 Claim, No Drawings

MEDIUM SPEED DIESEL ENGINE LUBRICATING OILS

This is a continuation of application Ser. No. 103,170 filed Sep. 30, 1987, now abandoned.

BACKGROUND OF THE INVENTION

1. Field of the Invention

This invention relates to lubricating oil compositions comprising minor amounts of a metal deactivator. More particularly, this invention relates to lubricating oil compositions for use in medium speed diesel engines, which compositions contain a reaction product that is rich in alkyl bis-3-amino-1,2,4-triazole.

2. Description of the Prior Art

Lubricating oil compositions for use in diesel engines are well known. Such compositions will contain one or more additives to improve their properties, e.g., additives which serve as anti-oxidants or corrosion inhibitors and additives which serve as metal deactivators.

Among the various types of diesel engines are the medium speed diesel engines, which are employed as stationary power sources, as marine diesel engines, e.g., engines used on river tow boats, and railroad locomotive engines. Particularly important are the medium speed railroad locomotive engines.

A number of lubricant additives are especially useful in lubricating oils to prevent sulfur induced corrosion of copper and copper alloys. For example, a highly effective metal passivator for use in lubricating oils that can be employed as crankcase oils for gasoline or diesel engines is the product of a reaction of 2,5-dimercapto-1,3,4-thiadiazole, sulfur dichloride, and an olefin containing 6 to 30 carbon atoms, as described by Lam in U.S. Pat. No. 4,487,706. Another example is a reaction product of a hydrocarbyl succinic anhydride in which the hydrocarbyl radical has from 12 to 30 carbon atoms and 5-amino triazole, as discussed by Sing, et al., in U.S. Pat. No. 4,256,595.

In U.S. Pat. Nos. 3,272,746 and 3,341,542, Le Seur, et al., disclose lubricating oil compositions containing acylated nitrogen compounds prepared, for example, by reacting a substituted succinic acid or derivative thereof with a nitrogen-containing compound, such as ammonia, aliphatic amines, aromatic amines, heterocyclic amines, or carboxylic amines. The resulting detergent composition comprises an oil-soluble, acylated nitrogen composition characterized by the presence within its structure of (A) a substantially hydrocarbon-substituted polar group selected from the class consisting of acyl, acylimidoyl, and acyloxy radicals wherein the substantially hydrocarbon substituent contains at least about 50 aliphatic carbon atoms and (B) a nitrogen-containing group characterized by a nitrogen atom attached directly to said relatively polar group. In Example 38 of these patents, polyisobutene-substituted succinic anhydride, aminoguanidine bicarbonate, and mineral oil were mixed and heated at a temperature of 130° C. (266° F.) to 165° C. (329° F.) for 5 hours. The residue was mixed with mineral oil and heated to 150° C. (302° F.) and filtered. The resulting product was used as a lubricating oil additive and found to be an effective dispersant. These patents teach that the mixture of acid-producing compound and the nitrogen-containing reactant is usually heated at a temperature above about 80° C. (176° F.), preferably, within the range of about 100° C. (212° F.) to about 250° C. (482° F.). These patents teach that guanidines are included in sources of nitrogen-containing compounds and present, as examples, guanidine, 1,3-diphenylguanidine, and 1,2,3-tributylguanidine. These patents do not indicate that the resulting product comprises triazoles. Furthermore, there is no suggestion that the product would be a suitable metal deactivator in an engine lubricant oil composition.

In U.S. Pat. No. 4,491,527, Lange, et al., disclose ester-heterocycle compositions useful as "lead paint" inhibitors and lubricants, e.g., compositions comprising a major proportion of a pentaerythritol ester of an alkenyl succinic acid in which the alkenyl group contains at least about 30 carbon atoms and a minor proportion of a heterocyclic condensation product of said alkenyl succinic acid derived from a 5-membered ring heterocycle containing at least 2 ring hetero atoms separated by a single carbon atom, at least one of said hetero atoms being nitrogen. The heterocyclic condensation product is characterized by the presence of at least one heterocyclic moiety including a 5- or 6-membered ring which contains at least 2 ring hetero atoms, separated by a single carbon atom. Such ring hetero atoms may be oxygen, sulfur, and nitrogen, with at least one thereof being nitrogen. Most often, the heterocyclic moiety contains a maximum of three ring hetero atoms and a 5-membered ring, preferably, a triazole or thiadiazole ring, and, most desirably, a 1,2,4-triazole ring. This patent teaches that aminoguanidine and salts of aminoguandine, such as aminoguanidine bicarbonate, are examples of acylic heterocycle precursors which may be reacted with the proper acid or acid derivative group. This patent does not suggest that a reaction product rich in an alkyl-substituted bis-3-amino-1,2,4-triazole would be a suitable metal deactivator in a medium speed diesel engine lubricating oil composition.

It has now been found that a reaction product of an alkyl-substituted dicarboxylic acid compound, e.g., a polybutenyl succinic anhydride, and a basic salt of amino-guanidine, e.g., aminoguanidine bicarbonate, which product comprises alkyl bis-3-amino-1,2,4-triazole, can be used in medium speed diesel engine oils, particularly, railroad locomotive diesel engine oils, protect metal engine parts, particularly, the copper and copper alloy parts.

According to the present invention, there is provided a lubricating oil composition for use in medium speed diesel engines, which composition provides reduced corrosion of metal engine parts and which composition comprises a major proportion of an oil of lubricating viscosity, particularly, a mid-range viscosity index (MVI) base oil, and a minor (metal deactivating) amount of a metal deactivator-dispersant that is rich in alkyl bis-3-amino-1-2,4-triazole. A suitable alkyl bis-3-amino-1,2,4-triazole is polybutenyl bis-3-amino-1,2,4-triazole. Typically, the metal deactivator-dispersant additive is present in an amount within the range of about 0.001 wt % to about 10 wt % based on the weight of the lubricating oil composition.

DESCRIPTION AND PREFERRED EMBODIMENTS

The presence of water and precursors of sludge in lubricating oils constitutes a very serious problem that is associated with crankcase lubricating oils. There occurs in the lubricating oil various foreign particles, such as dirt, soot, and products of decomposition that result from the breakdown of the lubricating oil. The combination of water and such foreign particles results in the deposition of sludge which has a deleterious effect upon the efficient operation of the engine containing the lubricating oil. In order to prevent the deposition of sludge, various detergents and dispersants are added to the lubricating oil composition.

There are various types of dispersants. For example, reaction products of a monocarboxylic acid, a dicarboxylic acid, a polycarboxylic acid, or derivatives thereof, with nitrogen-containing compounds, such as amines, are described in numerous patents. Examples of such patents are U.S. Pat. Nos. 3,163,603; 3,184,474; 3,215,707; 3,219,666; 3,271,310; and 3,272,746. Such reaction products are identified hereinafter as carboxylic polyamine dispersants.

There are those dispersants which comprise reaction products of aliphatic or alicyclic halides containing at least about 40 carbon atoms with amines, preferably, polyalkylene polyamines, examples of which dispersants are described in U.S. Pat. Nos. 3,275,554; 3,438,757; 3,454,555; and 3,565,804. Such dispersants can be identified as alkyl polyamine dispersants.

A third type of dispersants include those dispersants which comprise the reaction products of an alkyl phenol or an oxidized olefinic polymer, wherein the alkyl group is oil soluble, with aliphatic aldehydes containing 1 through 7 carbon atoms and amines, particularly alkylene polyamines. Such dispersants can be identified as Mannich polyamine dispersants and are described in such prior art as U.S. Pat. Nos. 2,459,112; 3,036,003; 3,355,270; 3,461,172; 3,442,808; 3,459,661; 3,544,470; 3,697,574; 3,591,598; 3,649,229; 2,726,882; and 4,011,380.

Another type of dispersants comprises dispersants comprising polymers containing an oil-solubilizing group, e.g., a pendant alkyl group having at least 8 carbon atoms, and a polar group, e.g., interpolymers of decyl methacrylate, vinyl decyl ether, or a relatively high molecular weight olefin with aminoalkyl acrylates, aminoalkyl acrylamides or poly-(oxyalkalene)-substituted alkyl acrylates, as well as copolymers of styrene, alkyl maleates, and maleic acid amides or imides, respectively. Such polymers can be identified as polymeric polyamine dispersants and are exemplified in U.S. Pat. Nos. 3,329,658; 3,449,250; 3,519,565; 3,666,730; 3,687,849; and 3,702,300.

Another type of dispersants includes those dispersants comprising products obtained by post-treating the carboxylic polyamine, alkyl polyamine, Mannich polyamine, or polymeric polyamine dispersants with such reagents as urea, thiourea, carbon disulfide, aldehydes, ketones, carboxylic acids, hydrocarbon-substituted succinic anhydrides, nitriles, epoxides, boron compounds, and phosphorus compounds. Such products are described in U.S. Pat. Nos. 3,036,003; 3,087,936; 3,200,107;1 3,282,955; 3,366,569; 3,502,677; 3,639,242; 3,649,229; 3,702,757; 3,704,308; and 3,708,522.

Descriptions and methods of preparation of the above-mentioned dispersants are adequately presented in the patents cited hereinabove. Those portions of these patents which are directed to descriptions of dispersants and their methods of preparation are incorporated by reference herein.

While detergents and dispersants can be added to the lubricating oil to maintain cleanliness in the engine and to minimize deposition of sludge, such dispersants sometimes provide a disadvantage. For example, polyamine dispersants are incompatible with the more recent flexible engine seals that are made up of fluorohydrocarbon compositions. These seals suitably prevent leakage of lubricants from the engine at points where moving parts, such as crankshafts, leave the engine. However, if engine seals that are prepared from fluorohydrocarbon compositions are utilized to seal engines containing lubricating oils having polyamine dispersants, the seals will be affected deleteriously by such dispersants. Mechanical deterioration, dimension deterioration, discoloration, crazing, and swelling of the seals occur. The polyamine-containing dispersants interact with the fluorohydrocarbon seals to alter the underlying polymeric structure. The composition of the seal absorbs oil and as the oil content of the seal increases the mechanical strength and dimensional integrity of the seal deteriorate to such an extent that the seal does not prevent leakage of lubricant from the crankcase.

As pointed out in the commonly-owned and co-pending patent application, U.S. Serial No., filed concurrently herewith, there is a dispersant that is a suitable lubricating oil additive and that is compatible with fluorohydrocarbon elastomers. This dispersant is prepared by reacting an alkyl-substituted dicarboxylic acid compound selected from the group consisting of alkyl-substituted dicarboxylic acids, alkyl-substituted dicarboxylic acid anhydrides, and mixtures thereof, such as a polybutenyl succinic acid compound, e.g. polybutenyl succinic anhydride (PSA), and a basic salt of aminoguanidine, e.g., aminoguanidine bicarbonate (AGB), in specific amounts to form a mixture of products. When PSA is reacted with AGB, the principal product is polybutenyl bis-3-amino-1-2,4-triazole. Apparently, the aromatic character of the triazole ring reduces sufficiently the basicity of the amine, even though a high-nitrogen content is present, in order that the dispersant and the fluorohydrocarbon composition are sufficiently compatible for concurrent use in internal combustion engines.

As shown in the examples presented hereinafter, this dispersant has been found to be an excellent metal deactivator when used in medium speed diesel engines, such as those employed as stationary power sources for generating electrical power, marine diesel engines, and railroad locomotive diesel engines.

According to the present invention, there is provided a lubricating oil composition for use in medium speed diesel engines, which composition comprises an oil of lubricating viscosity and a minor amount of a dispersant that is rich in an alkyl bis-3-amino-1,2,4-triazole, said dispersant being the reaction product obtained by reacting an alkyl-substituted dicarboxylic acid compound selected from the group consisting of alkyl-substituted dicarboxylic acids, alkyl-substituted dicarboxylic acid anhydrides, and mixtures thereof, with a basic salt of aminoguanidine under conditions that will provide a product that is rich in said alkyl bis-3-amino-1,2,4-triazole.

A "minor" amount of the dispersant signifies a metal-deactivator amount thereof. Such an amount is within the range of about 0.001 wt % to about 10 wt %, based on the weight of the lubricating oil composition. Preferably, the amount is within the range of about 0.005 wt % to about 2 wt % and, more preferably, the amount is within the range of about 0.01 wt % to about 0.5 wt %, based on the weight of the lubricating oil composition.

The phrase "rich in an alkyl bis-3-amino-1,2,4-triazole" means that the alkyl bis-3-amino-1,2,4-triazole is present in an amount that is sufficient to provide at least some metal deactivation.

One of the reactants employed in the process of the present invention is an alkyl-substituted dicarboxylic acid compound selected from the group consisting of alkyl-substituted dicarboxylic acids, alkyl-substituted dicarboxylic acid anhydrides, and mixtures thereof. Such substituted dicarboxylic acid compound is prepared normally by the alkylation of an unsaturated acid, an anhydride of such acid, or a mixture thereof with homopolymers and interpolymers of polymerizable olefin monomers containing up to about 10 carbon atoms. Such polymers are produced typically from ethylene, propylene, 1-butene, 2-butene, isobutene, 1-hexene, or 1-octene and have at least 30 carbon atoms in a chain. They are preferably produced from polybutenes. Suitable polybutenes can be purchased from Amoco Chemical Company under the INDOPOL trade name. Polypropene can be obtained from Amoco Petroleum Additives Company.

The alkyl radical can be any oil-solubilizing organic radical. For example, it can be any hydrocarbon group having from 1 to 200 carbon atoms, saturated or unsaturated. It can be an alkenyl group derived from polyisobutylene of molecular weight in the range of 250 to 5000. It can be an alkenyl group derived from polypropylene or polyethylene of molecular weight in the range of 200 to 5000. It can be alkyl groups derived from the "dimer acids" or dimerized fatty acids having carbon atoms within the range of 8 to 30 carbon atoms, some acids of which may contain unsaturation, for example, those derived from oleic or linoleic acids. It can be an alkyl group derived from linear or branched alkenes having from 4 to 30 carbon atoms, for example, n-dodecyl, t-dodecyl, t-nonyl, or t-octyl.

Typically, the chain of carbon atoms in the substituent ranges from about 30 carbon atoms to about 200 carbon atoms, or higher; preferably, from about 50 carbon atoms to about 200 carbon atoms; and, more preferably, from about 60 carbon atoms to about 160 carbon atoms.

The acids that are contemplated for use in making the desired dicarboxylic acid compounds are unsaturated. Such acids, and derivatives thereof, as acrylic acid, methacrylic acid, maleic acid, maleic anhydride, citraconic acid, and citraconic anhydride are contemplated. Other possible dicarboxylic acid sources are malonic acid, glutaric acid, adipic acid, and alkylated aromatic dicarboxylic acids, e.g, phthalic acid. The acid that is employed, when used in the specified amount relative to that of AGB, must provide a final product that is rich in alkyl bis-3-amino-1,2,4-triazole. A preferred acid and its anhydride are succinic acid and succinic anhydride.

For convenience only, the following discussion will be directed to the use of polybutenyl succinic anhydride (PSA) as the alkyl-substituted dicarboxylic acid compound. The PSA was reacted with aminoguanidine bicarbonate (AGB) in the examples which are discussed hereinafter. It will be shown that the reaction between PSA and AGB was conducted at more than one relative ratio of reactants. The products were examined for their infrared spectra and for their dispersant properties in various dispersant tests and their dispersant performances were compared to the performance of a commercial Mannich dispersant.

In one instance, one mole of PSA was reacted with one mole of AGB. The resulting product produced an infrared spectrum having a dominant peak at 1735 cm-1 with a shoulder at 1700 cm$^{-1}$. The dispersant tests demonstrated that this product did not perform as well as the commercial Mannich dispersant.

On the other hand, when one mole of PSA was reacted with two moles of AGB, the product presented an infrared spectrum having a dominant peak at 1640 cm$^{-1}$, smaller peaks at approximately 1700 cm$^{-1}$, and characteristic "N-H" stretching bands at 3200-3500 cm$^{-1}$. This product perstretching formed as well as the commercial Mannich dispersant did. The use of spectra of known compounds resulted in the revelation that the product was principally a triazole. The stoichiometry would suggest primarily a bistriazole having the following structure:

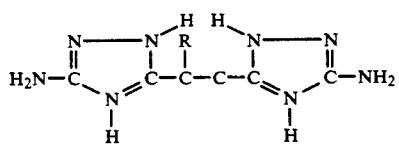

This structure is that of polybutenyl bis-3-amino-1,2,4-triazole. Such a product contains a relatively high nitrogen content, within the range of about 1.8 wt % to about 2.9 wt % nitrogen, when compared to that of the commercial Mannich dispersant, namely, 1.15 wt % nitrogen.

The five-membered ring of the triazoles is considered to be aromatic. Depending upon the salt formed, the aminotriazole will exhibit both acidic and basic properties. The aminotriazoles are fairly stable to oxidizing agents and are extremely resistant to hydrolysis.

With no intention of being bound, it is proposed that the reaction of one mole of PSA with two moles of AGB will result in the formation of a diamide, which can be seen in the infrared spectrum at the early stages of the reaction. In the presence of base, i.e., the carbonate, cyclization can occur easily to the five-membered triazole ring. During the cyclization, water and carbon dioxide are evolved.

The desired product can be obtained conveniently by reacting PSA and AGB in appropriate amounts at a temperature within the range of about 155° C. (311° F.) to about 200° C. (392° F.), preferably, within the range of about 170° C. (338° F.) to about 190° C. (374° F.), and at atmospheric pressure. Of course, the reaction could be carried out at subatmospheric pressure or superatmospheric pressure. In either case, the range of temperatures would be different from those listed for the reaction that is carried out at atmospheric pressure. The ratio of reactants is within the range of about 1.6 moles of AGB per mole of PSA to about 2 moles of AGB per mole of PSA, preferably, within the range of about 1.7 moles of AGB per mole of PSA to about 2 moles of AGB per mole of PSA. The reaction is carried out for a period of time within the range of about 1 hour to about 4 hours, preferably, within the range of about 2 hours to about 4 hours.

The polybutenyl succinic anhydride can be prepared by reacting maleic anhydride with a high molecular weight olefin or a chlorinated hydrocarbon, such as an olefin polymer of 1-butene or 2-butene, at a temperature within the range of about 100° C. (212° F.) to about 200° C. (392° F.).

The aminoguanidine and its bicarbonate salt can be obtained from commercial suppliers. For example, the aminoguanidine bicarbonate salt can be obtained from Nippon Carbide Industries Co., Inc.

The lubricating oil compositions of the present invention can contain in addition to the metal deactivator-dispersant other additives, such as other dispersants, ash-containing detergents, pour point depressing agents, viscosity index improving agents, extreme pressure agents, rust inhibitors, oxidation inhibitors, corrosion inhibitors, and anti-form agents. Such additives are well known to those skilled in the art and will not be discussed further herein.

The metal deactivator-dispersant and the various other additives can be conveniently added to the base oil and blended therein.

The following examples are being presented to aid in the understanding of the present invention. They are being presented for the purpose of illustration only and are not intended to limit the scope of the present invention.

EXAMPLE 1

In this example, an embodiment of the dispersant of the present invention was prepared. Into a three-liter, three-necked, round-bottom flask, 1000 g of 57.5% active polybutenyl succinic anhydride (0.25 mole), 69.9 g of 98.5% aminoguanidine bicarbonate (0.50 mole), and 494 g of a base oil were placed under nitrogen. The polybutenyl succinic anhydride had been prepared by reacting maleic anhydride with an H-1500 INDOPOL polybutene having a number average molecular weight ($M_n$) of about 2060, obtained from Amoco Chemical Company. The mixture, under constant stirring, was heated for three hours at a temperature of 188° C. (370° F.) to form the polybutenyl bis-3-amino-1,2,4-triazole. The product was filtered to provide a 40% active polybutenyl bis-3-amino-1,2,4-triazole dispersant, identified hereinafter as Dispersant No. 1.

In a similar manner, a second embodiment of the dispersant of the present invention was prepared. In this preparation, the polybutenyl succinic anhydride was prepared by reacting maleic anhydride with H-300 INDOPOL polybutenes having a $M_n$ of about 1290. These H-300 INDOPOL polybutenes were obtained from Amoco Chemical Company. The resulting polybutenyl bis-3-amino-1,2,4-triazole dispersant is identified hereinafter as Dispersant No. 2.

Each of these two dispersants was tested in both the spot dispersancy test (SDT) and the oil thickening spot dispersancy test [OTT(SDT)].

The spot dispersancy test measures the movement of insoluble particles chromatographically along blotter paper in used motor oil. When a dispersant candidate is added to used oil, movement along the paper results in two rings. The inner ring constitutes the sludge being transported by the dispersant; the outer ring comprises the base oil. The effectiveness of the dispersant is defined by the ratio of the inner ring to the outer ring. The higher the value of this ratio for a particular candidate, the better the performance of that candidate as a disperant. The oil thickening test is an analogous test in which the dispersant is tested in an oil that is being oxidized and the spot dispersancy test indicates the effect of this oxidation with time.

For comparison, a typical commercial Mannich dispersant, identified as Dispersant No. 3, was also subjected to these tests.

The results of these tests are presented hereinbelow in Table I.

TABLE I

| Dispersant | Dispersant Performance | | | | | | | |
|---|---|---|---|---|---|---|---|---|
| | SDT % | | | | OTT (SDT) Time, hr | | | |
| | 0 | 2 | 4 | 6 | 24 | 48 | 56 | 72 |
| 1 | 37 | 46 | 85 | 84 | 100 | 93 | 90 | 42 |
| 2 | 37 | 58 | 85 | 86 | 100 | 90 | 75 | 34 |
| 3 | 37 | 60 | 84 | 88 | 100 | 88 | 69 | 28 |

These results indicate that the two embodiments of the dispersant of the present invention perform in the SDT and OTT in a manner similar to that of the reference Mannich dispersant.

In the following examples, various lubricating oil compositions employing mid-range viscosity index (MVI) base oils were tested in a modified Union Pacific Oxidation Test for oxidation stability and corrosion control.

This modified test was conducted in a Sargent-Welch S-67424-Z Viscometer Bath with temperature controller. The test tube, tube, oxygen inlet tube, and condenser were similar to those employed in ASTM test method D943. The metal coupons used in the test were obtained from the Metaspec Co. of San Antonio, Tex., U.S.A. The copper coupons were each 1 in.×1 in.×0.125 in. and were made of electrolytic alloy No. 110 QQ-C-576. The steel coupons were each 1 in.×1 in.×0.125 in. and were fabricated of low-carbon, QQ-S-698 Gr 1009 cold rolled No. 4 temper steel. Optional lead coupons were not employed in these tests. The coupons, which had two 1/16-in. holes drilled therefrom, were tied together with clean pieces of cotton cord around the inlet tube. Prior to use, the metal coupons were polished with a fine emery cloth (240 grit) and subsequently with No. 0 steel wool until a clean and smooth surface was obtained. The polished coupons were rinsed with hexane and allowed to dry in air prior to being weighed. The coupons were then tied together in the shape of a hollow prism and placed on the Pyrex support of the oxygen inlet tube.

A 300 g sample of the candidate test oil was weighed into the test tube. The oxygen inlet tube with the test coupons was then inserted into the test tube and the test tube assembly was placed in the oil bath, which had been preheated to a temperature of 300° F. (149° C.) ±2. Oxygen was passed through the test sample at a flow rate of 5±0.2 liters per hr. for a normal test period of 72 hr., unless other noted.

At the termination of the test period, oxygen flow was stopped, the test tube assembly and condenser were removed from the oil bath, the coupons were removed from the assembly, washed with hexane and acetone, air dried, and weighed for weight losses. The oxidized oil sample was submitted for various analyses, such as viscosity and the amount(s) of one or more metals, e.g., copper, in the oil. The weight loss would indicate the amount of corrosion that had occurred. Alternatively, the amount of the metal in the oil, e.g., copper and/or iron, would indicate the amount of corrosion that had occurred.

EXAMPLE 2

In this example, an experimental lubricating oil composition containing polybutenyl bis-3-amino-1,2,4-triazole, identified hereinafter as Sample No. 1, was compared with three commercial railroad engine oils (Samples 2, 3 and 4). The lubricating oil composition Sample No. 1, which contained an embodiment of the dispersant of the present invention, was prepared as described hereinabove in Example 1. An H-1500 INDOPOL polybutene having a $M_n$ of about 2060, obtained from Amoco Chemical Company, was used in this preparation.

Sample No. 1, corresponding to the present invention, contained 3 wt % bis-3-amino-1,2,4-triazole, 5 wt % calcium Mannich phenate oxidation inhibitor and detergent, 1.6 wt % high-base sulfurized calcium phenate inhibitor and detergent, 1.0 wt % low-base calcium sulfonate detergent, 0.5 wt % Chlorowax 40, and the remainder base oil.

Each of the above additives was blended with base oil and tested in the modified Union Pacific Oxidation Test as described hereinabove for their oxidation stability and corrosion control. The oxidation stability is expressed in terms of "% viscosity increase at 40° C." The extent to which the viscosity of the oil increases is an indication of the oxidation stability of the lubricant being used in the oil. The greater the increase in viscosity, the less stable that particular oil is to oxidation.

Furthermore, the weight loss of the test strip calculated as the metal in the oil is a measure of the extent to which corrosion inhibition has been effected. The greater the amount of a particular metal in the oil, the smaller is the corrosion inhibition of the additive in that oil.

The results of these tests are presented hereinbelow in Table II.

TABLE II

Comparison of Sample No. 1 with Commercial Railroad Diesel Oils

| | Sample No. | | | |
|---|---|---|---|---|
| | 2 | 3 | 4 | 1 |
| % Viscosity Increase at 40° C. | 29.9 | 30.7 | 54.1 | 14.7 |
| Cu in Oil, ppm (wt) | 5.2 | 11.9 | 18.2 | 1.9 |
| Fe in Oil, ppm (wt) | 3.3 | 3.0 | 3.3 | 1.7 |

(1) Exp = Experimental

These results demonstrate that a medium speed diesel oil composition that contains a polybutenyl bis-3-amino-1,2,4-triazole provides better corrosion inhibition than the tested commercial railroad locomotive engine oils (Samples 2, 3 and 4). Oxidation stability, as evidenced by viscosity increase, is also better.

EXAMPLE 3

In this example, various lubricating oils containing formulations comprising an embodiment of the corrosion inhibitor triazole dispersant of the present invention, identified hereinafter as "TD", and a typical commercial Mannich dispersant, were tested in the modified Union Pacific Oxidation Test for their abilities to furnish corrosion inhibition. Each formulation contained a total of 3 wt % dispersant material. The samples ranged from 3 wt % TD and 0 wt % commercial Mannich dispersant to 0 wt % TD and 3 wt % commercial Mannich dispersant. The TD was prepared as described in Example 1 hereinabove and was made with H-1500 INDOPOL polybutene having a $M_n$ of about 2060, which was obtained from Amoco Chemical Company. Each experimental formulation also contained 5 wt % calcium Mannich phenate oxidation inhibitor and detergent, 1.6 wt % high-base sulfurized calcium phenate inhibitor/detergent 1.0 wt % low-base calcium sulfonate detergent, 0.5 wt % of Chlorowax 40, and the remainder base oil. The combination of bis-3-amino-1,2,4-triazole and 3 wt % of Detergent A to 3 wt % bis-3-amino-1,2,4-triazole and 0 wt % Detergent A. These samples were tested in the modified Union Pacific Oxidation Test for their corrosion inhibition expressed in terms of loss in weight of the copper coupon. The results of these tests are presented hereinbelow in Table III.

TABLE III

TD Concentration Studies

| | Sample No. | | | | | | | | |
|---|---|---|---|---|---|---|---|---|---|
| | 1 | 5 | 6 | 7 | 8 | 9 | 10 | 11 | 12 |
| Formulation | | | | | | | | | |
| Wt % TD | 3.0 | 2.0 | 1.0 | 0.5 | 0.25 | 0.175 | 0.10 | 0.05 | 0.0 |
| Wt % Mannich | 0.0 | 1.0 | 2.0 | 2.5 | 2.75 | 2.825 | 2.90 | 2.95 | 3.0 |
| % Viscosity Increase at 40° C. | 14.7 | 14.0 | 12.1 | 12.5 | 11.4 | 12.8 | 16.4 | 23.3 | 30.6 |
| Copper Coupon Wt Loss, mg | 0.5 | 0.5 | 0.6 | 1.0 | 1.1 | 1.4 | 2.2 | 4.1 | 6.3 |

The results presented in Table III demonstrate corrosion inhibition resulted from the use of the present invention.

EXAMPLE 4

An embodiment of the lubricating oil composition of the present invention, Sample No. 1, which contained 3 wt % of the dispersant of the present invention prepared with H-1500 INDOPOL polybutene having a $M_n$ of about 2060 and obtained from Amoco Chemical Company, was compared with a formulation containing 0.05 wt % REOMET 39 and with an experimental prototype formulation containing 0.05 wt % REOMET 39. REOMET 39, a triazole derivative, was obtained from Ciba-Geigy Company. It is believed to be an alkylated 1,2,3-benzotriazole. Each oil sample contained AMOCO MVI oil as the base oil. The commercial formulation, obtained from Amoco Petroleum Additives Company, is identified as Sample No. 13 hereinafter. The experimental formulation is identified as Sample No. 14. Each of Sample Nos. 1 and 14 contained, in addition to the metal deactivator listed and the MVI base oil, 5 wt % calcium Mannich phenate oxidation inhibitor-detergent, 1.6 wt % high-base sulfurized calcium phenate inhibitor-detergent, 1.0 wt % low-base calcium sulfonate detergent, and 0.5 wt % Chlorowax 40.

The comparison was made via the modified Union Pacific Oxidation Test described hereinabove. The results are presented in Table IV.

TABLE IV

Comparison with REOMET 39

| | Sample No. | | |
|---|---|---|---|
| | 13 | 14 | 1 |
| Formulation | 0.05% REOMET 39 | Exp.-0.05% REOMET 39 | Exp.-3 wt % Invention |
| % Viscosity Increase at 40° C. | 45.6 | 33.0 | 14.7 |
| Copper in Oil, ppm (wt) | 18.2 | 24.4 | 1.9 |
| Iron in Oil, ppm (wt) | 3.0 | 1.7 | 1.7 |

The results of this table show that the lubricating oil composition of the present invention, Sample No. 1, provided significantly greater corrosion inhibition than did the two compositions that contained REOMET 39.

EXAMPLE 5

In this example, different embodiments of the dispersant of the present invention contained alkyl bis-3-amino-1,2,4-triazoles having alkyl radicals with different numbers of carbon atoms than the alkyl bis-3-amino-1,2,4-triazoles in the other embodiments. Each of the samples in this example was a MVI oil and was made with AMOCO MVI base oil and each contained 3 wt % dispersant of the present invention, 5 wt % calcium-Mannich phenate oxidation inhibitor and detergent, 1.6 wt % high-base sulfurized calcium phenate inhibitor-detergent, 1.0 wt % low-base calcium sulfonate detergent, 0.5 wt % Chlorowax 40, and 88.9 wt % base oil.

An H-1500 INDOPOL polybutene having a $M_n$ of about 2060 and obtained from Amoco Chemical Company was used to prepare the PSA that was reacted with AGB to make Product No. 1 and Product No. 4. An H-300 INDOPOL polybutene having a $M_n$ of about 1290 and obtained from Amoco Chemical Company was used to prepare the PSA that was employed to make Product No. 2. A C20-polypropene having a $M_n$ of about 550 and obtained from Amoco Petroleum Additives Company was used in the preparation of the PSA that was employed to make Product No. 3. The preparations were similar to those described in Example 1 hereinabove.

Each of the products was blended into its oil sample and the resulting oil sample was subjected to the modified Union Pacific Oxidation Text described hereinabove. The results of these tests are presented hereinbelow in Table V.

TABLE V

Effect of Size of Alkyl Radical

| | Product No. | | | |
|---|---|---|---|---|
| | 1 | 2 | 3 | 4 |
| Oil Sample No. | 15 | 16 | 17 | 1 |
| % Viscosity Increase at 40° C. | 14.6 | 14.8 | 17.3 | 14.7 |
| Copper in Oil, ppm (wt) | 1.9 | 2.0 | 2.1 | 1.9 |
| Iron in Oil, ppm (wt) | 1.9 | 1.8 | 1.9 | 1.8 |

The results of the tests in this example demonstrate that these different embodiments of the present invention provided comparable oxidation resistance and comparable metal protecting activity. The length of side chain or alkyl radical did not appear to deleteriously affect the product's performance.

From the above test data, it is shown that lubricating oil compositions of the present invention furnish improved metal passivation. The dispersant compound of these compositions is shown to be a very effective metal deactivating agent, especially for copper. It appears that such component is effective in chlorine-containing formulations as a metal deactivator. The use of this metal deactivator-dispersant, which is rich in alkyl bis-3-amino-1,2,4-triazole, provides a unique metal deactivating function in superior medium speed diesel engine oils.

What is claimed is:

1. A method for providing improved oxidation stability and for protecting copper and copper alloy parts in a medium speed diesel engine which method comprises lubricating the engine with a composition comprising an oil of lubricating viscosity and a minor amount of a metal deactivator-dispersant consisting essentially of alkyl bis-3-amino-1,2,4-triazole, said metal deactivator-dispersant being the reaction product obtained by reacting an alkyl-substituted dicarboxylic acid compound selected from the group consisting of alkyl-substituted dicarboxylic acids, alkyl-substituted dicarboxylic acid anhydrides, and mixtures thereof, with a basic salt of amino-guanidine at a temperature in the range of about 180° to about 200° C. whereby said reaction product consists entirely of said triazole.

* * * * *